(12) United States Patent
Drennan

(10) Patent No.: US 7,758,481 B2
(45) Date of Patent: Jul. 20, 2010

(54) DYNAMIC HIP STABILIZER

(76) Inventor: Denis Burke Drennan, 4 Milburn Park, Evanston, IL (US) 60201

( * ) Notice: Subject to any disclaimer, the term of this patent is extended or adjusted under 35 U.S.C. 154(b) by 558 days.

(21) Appl. No.: 11/533,429

(22) Filed: Sep. 20, 2006

(65) Prior Publication Data

US 2007/0027419 A1 Feb. 1, 2007

Related U.S. Application Data

(63) Continuation-in-part of application No. 10/604,993, filed on Aug. 29, 2003, now Pat. No. 7,476,185.

(60) Provisional application No. 60/319,519, filed on Sep. 4, 2002.

(51) Int. Cl.
*A63B 21/00* (2006.01)

(52) U.S. Cl. .................. 482/124; 482/121

(58) Field of Classification Search ......... 482/121, 482/124, 51; 601/33, 131
See application file for complete search history.

(56) References Cited

U.S. PATENT DOCUMENTS

| | | | |
|---|---|---|---|
| 976,564 A | 11/1910 | Odson | |
| 1,722,192 A | 7/1929 | Brokaw | |
| 2,035,010 A * | 3/1936 | Rawlings | ............... 601/23 |
| 2,332,119 A | 10/1943 | Springer | |
| 4,524,760 A | 6/1985 | Lerner | |
| 4,531,515 A | 7/1985 | Rolfes | |
| 4,709,692 A | 12/1987 | Kirschenberg et al. | |
| 4,901,710 A | 2/1990 | Meyer | |
| 4,905,678 A | 3/1990 | Cumins et al. | |
| 4,926,845 A | 5/1990 | Harris | |
| 5,207,635 A * | 5/1993 | Richards et al. | ............... 602/19 |
| 5,267,928 A | 12/1993 | Barile et al. | |
| 5,465,428 A | 11/1995 | Earl | |
| 5,573,487 A * | 11/1996 | Wallner | ..................... 482/124 |
| 5,720,042 A | 2/1998 | Wilkinson | |
| 5,840,050 A | 11/1998 | Lerman | |
| 5,893,367 A | 4/1999 | Dubats et al. | |
| 5,928,175 A | 7/1999 | Tanaka | |
| 6,039,707 A | 3/2000 | Crawford et al. | |
| 2003/0092545 A1 * | 5/2003 | Koscielny et al. | ........... 482/124 |
| 2004/0116260 A1 | 6/2004 | Drennan | |

OTHER PUBLICATIONS

Eur Med Rehabilitation Center, Dec. 1992.

* cited by examiner

*Primary Examiner*—Jerome Donnelly
(74) *Attorney, Agent, or Firm*—Hartman & Hartman P.C.; Gary M. Hartman; Domenica N. S. Hartman

(57) ABSTRACT

A dynamic hip stabilizer utilized to reduce the risk of post-operative and recurrent traumatic hip dislocations. The hip stabilizer includes a pelvic girdle, at least one thigh cuff, and one or more elements for generating an elastic tensile force between the girdle and cuff. The girdle has an upper portion configured for defining an upper opening for the wearer's waist, a lower portion configured for defining a lower opening for the wearer's hips, and a posterior portion configured for engaging the wearer's lower back. The hip stabilizer further includes one or more elements for engaging the wearer's shoulders to limit movement of the girdle toward the thigh cuffs caused by the elastic tensile force, and one or more elements for stiffening the posterior portion of the girdle.

22 Claims, 4 Drawing Sheets

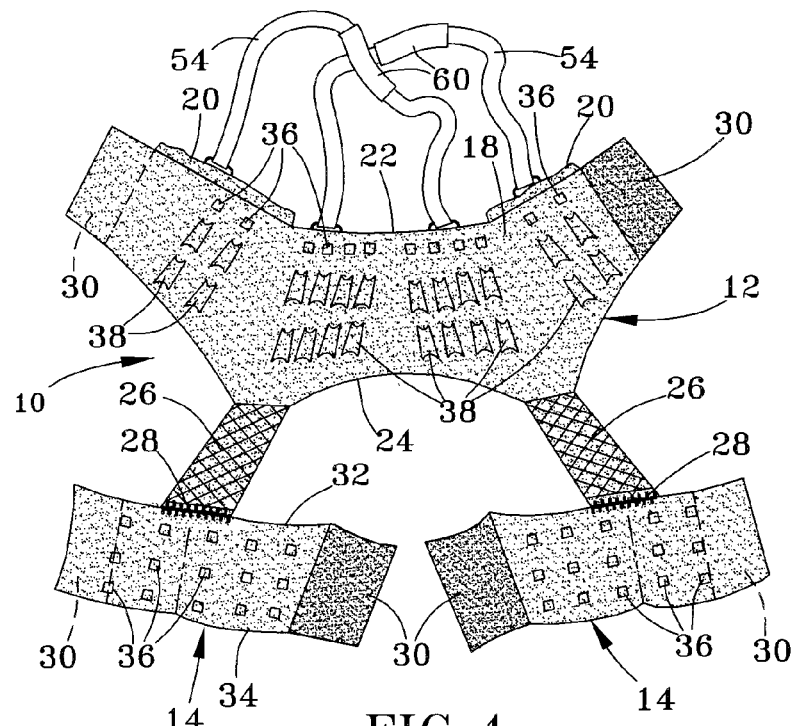
FIG.4
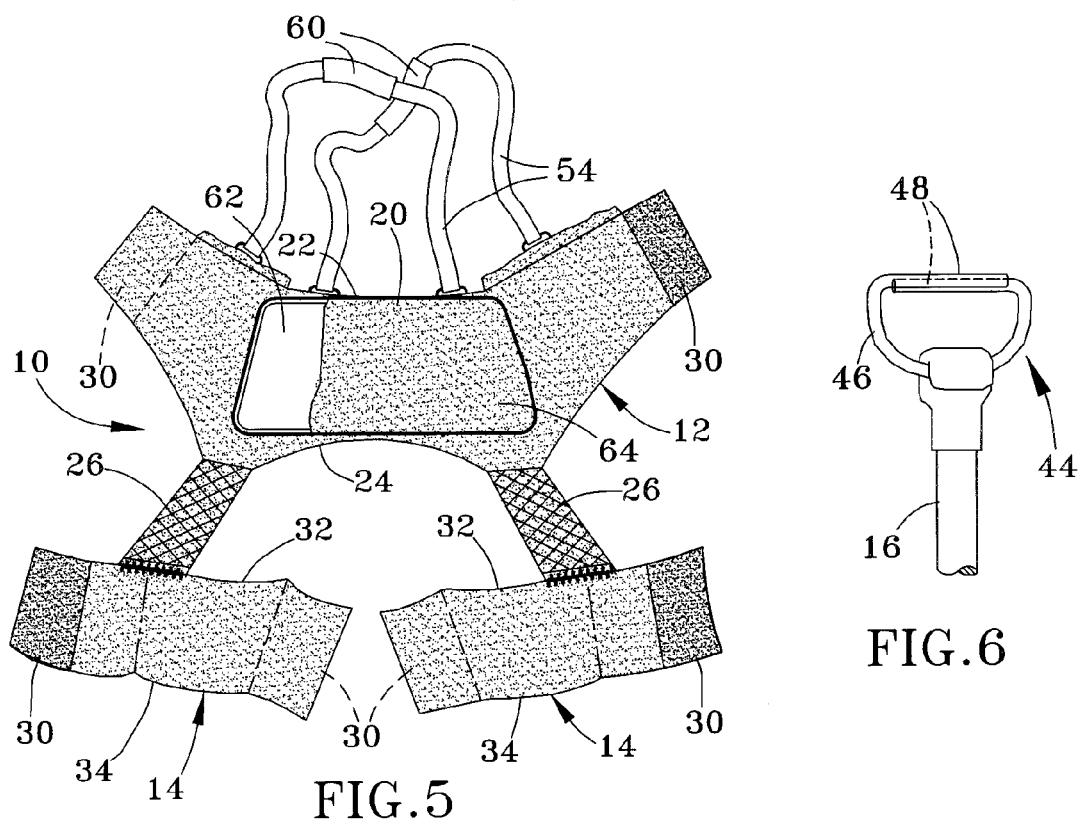
FIG.5
FIG.6

DYNAMIC HIP STABILIZER

CROSS REFERENCE TO RELATED APPLICATIONS

This is a continuation-in-part patent application of co-pending U.S. patent application Ser. No. 10/604,993, filed Aug. 29, 2003, which claims the benefit of U.S. Provisional Application No. 60/319,519, filed Sep. 4, 2002. The contents of these prior applications are incorporated herein by reference.

BACKGROUND OF THE INVENTION

The present invention relates to devices utilized to reduce the risk of postoperative hip dislocations and recurrent traumatic hip dislocations. More particularly, this invention relates to a dynamic hip stabilizer with a combination of components that generate tensile (tensional) forces capable of holding a patient's thigh to the patient's pelvis, preferably with enough tension to control excessive adduction, flexion or extension, control excessive internal or external rotation, provide hip stability by controlling and modifying certain hip motions through increasing tension as the extremes of a particular motion are approached, and provide hip stability by constantly maintaining elevated abductor tension across the hip joint.

There are a variety of techniques currently in use to prevent postoperative hip dislocations, recurrent traumatic hip dislocations, etc., some of which make use of specialized devices. A basic technique is to place a pillow between the thighs of the patient to cause abduction of the hips. A slightly more advanced technique is to secure a foam abduction pillow between the thighs with hook and loop straps to hold the hips in wide abduction. More advanced techniques include the use of single hip spica abduction braces, which generally comprise a thermoplastic waist brace attached to a thermoplastic thigh component by a hinged metal bar. The metal hinge portion allows flexion of the hip within a variable fixed range which can be set by the treatment provider. Single and bilateral hip spica casts, which serve to prevent all hip motions, also have long been used. Another type of device is the hip abduction brace, which generally comprises two curved semicircular plastic plates connected by hinges to a central threaded expansion-contraction device. By turning a central control threaded screw, the semicircular plastic plates spread out. When held between the proximal thighs by hook and loop straps, the device pushes the thighs apart, attempting to maintain abduction of the hips.

Various shortcomings are associated with the use of the above techniques and devices. Conventional pillows are too moveable and not wide enough to give consistent abduction, and undesirably allow the patient to move about. As a result, a pillow is rarely capable of preventing postoperative dislocation because it does not move with the patient who rolls over, or when the patient sits at the side of the bed or is being transferred to a wheel chair. Foam abduction pillows are clumsy and require considerable nursing effort to roll a patient from side to side. Furthermore, foam abduction pillows must be removed when the patient sits up and when bed-to-chair transfers are required.

A significant shortcoming of hip spica casts is the risk of prolonged stiffness because of the lack of all motion at the hip for many weeks. While single hip spica abduction braces avoid this concern, they require measurement and fitting by an orthotist and are formed from prefabricated parts of thermoplastic material and metal struts. Though single hip spica abduction braces can be worn in bed and while the patient sits and is being transferred, form-fit plastic abdominal and thigh portions of the brace often do not fit well, and allow many patients to rotate, putting the hip at risk. These braces also often allow some adduction and internal rotation, which is a significant risk to hip stability. Furthermore, this type of brace offers no compression of the femur against the pelvic acetabulum.

Hip abduction braces work reasonably well for the first days after surgery when the patient is fairly inactive. However, if not maintained in its fully abducted position, this type of brace allows for adduction to neutral and flexion is uncontrolled. The brace is removed for perineal care and when sitting the patient up at bedside. In addition, this type of brace cannot be worn during patient bed-to-wheelchair transfers or during gait training.

Other techniques and braces that pertain to the prevention of hip dislocations, or more generally to supporting or bracing the hip region, include U.S. Pat. No. 976,564 to Goodson, U.S. Pat. No. 1,722,192 to Brokaw, U.S. Pat. No. 2,332,119 Springer, U.S. Pat. No. 4,531,515 to Rolfes, U.S. Pat. No. 4,709,692 to Kirschenberg et al., U.S. Pat. No. 4,901,710 to Meyer, U.S. Pat. No. 4,905,678 to Cumins et al., U.S. Pat. No. 4,926,845 to Harris, U.S. Pat. No. 5,267,928 to Barile et al., U.S. Pat. No. 5,286,251 to Thompson et al., U.S. Pat. No. 5,465,428 to Earl, U.S. Pat. No. 5,840,050 to Lerman, U.S. Pat. No. 5,893,367 to Dubats et al., U.S. Pat. No. 5,928,175 to Tanaka, and U.S. Pat. No. 6,039,707 to Crawford et al. Each of Goodson, Brokaw, Barile et al. and Earl entail device with a waist portion, thigh portions, and elastic straps that interconnect the waist and thigh portions. Goodson's straps are limited to the posterior to provide posture support. Brokaw discloses a brace with inelastic anterior straps and elastic posterior straps. Barile et al. disclose a one-piece support garment with elastic anterior and posterior straps and elastic lateral straps, the latter of which may be wrapped in various ways around the thighs or hips of the wearer. Finally, Earl discloses an exercise device whose elastic straps are limited to the posterior side of the device.

It would be desirable if an improved device was available that was specifically configured to prevent hip dislocations by controlling excessive adduction, flexion and/or extension, controlling excessive internal or external rotation, and increasing hip stability.

BRIEF SUMMARY OF THE INVENTION

The present invention provides a dynamic hip stabilizer capable of reducing the risk of hip dislocations, including postoperative and recurrent traumatic hip dislocations. The hip stabilizer generally comprises a pelvic girdle, at least one thigh cuff, and one or more elements for generating an elastic tensile force between the pelvic girdle and the thigh cuff. The pelvic girdle has an upper portion configured for defining an upper opening for the wearer's waist, a lower portion configured for defining a lower opening for the wearer's hips, and a posterior portion configured for engaging the wearer's lower back when the pelvic girdle is worn by the wearer. The thigh cuff defines lower and upper openings for the wearer's thigh. The hip stabilizer further includes one or more elements for engaging the wearer's shoulders to limit movement of the pelvic girdle toward the thigh cuff caused by the elastic tensile force, and one or more elements for stiffening the posterior portion of the pelvic girdle relative to the upper and lower portions of the pelvic girdle.

According to a preferred aspect of the invention, the elastic tensile force generated between the pelvic girdle and thigh cuff is operative to hold the wearer's thigh to the wearer's pelvis with sufficient tension to control excessive adduction, flexion or extension, provide hip stability by controlling and modifying certain hip motions through increasing tension as the extremes of a particular motion are approached, and provide hip stability by constantly maintaining elevated abductor tension. The stability and proper positioning of the girdle is enhanced by the action of the one or more elements that limit movement of the girdle toward the thigh cuff, and by the one or more stiffening elements that also provide support to the lower back of the wearer.

Other objects and advantages of this invention will be better appreciated from the following detailed description.

BRIEF DESCRIPTION OF THE DRAWINGS

FIGS. 4 and 5 are plan views of the exterior and interior surfaces, respectively, of the pelvic girdle and thigh cuffs shown in FIGS. 1, 2 and 3.

FIG. 6 is an enlarged view of a D-shaped ring for attaching an elastic cable that interconnects the pelvic girdle to a thigh cuff of the preceding Figures.

DETAILED DESCRIPTION OF THE INVENTION

Figure 1:
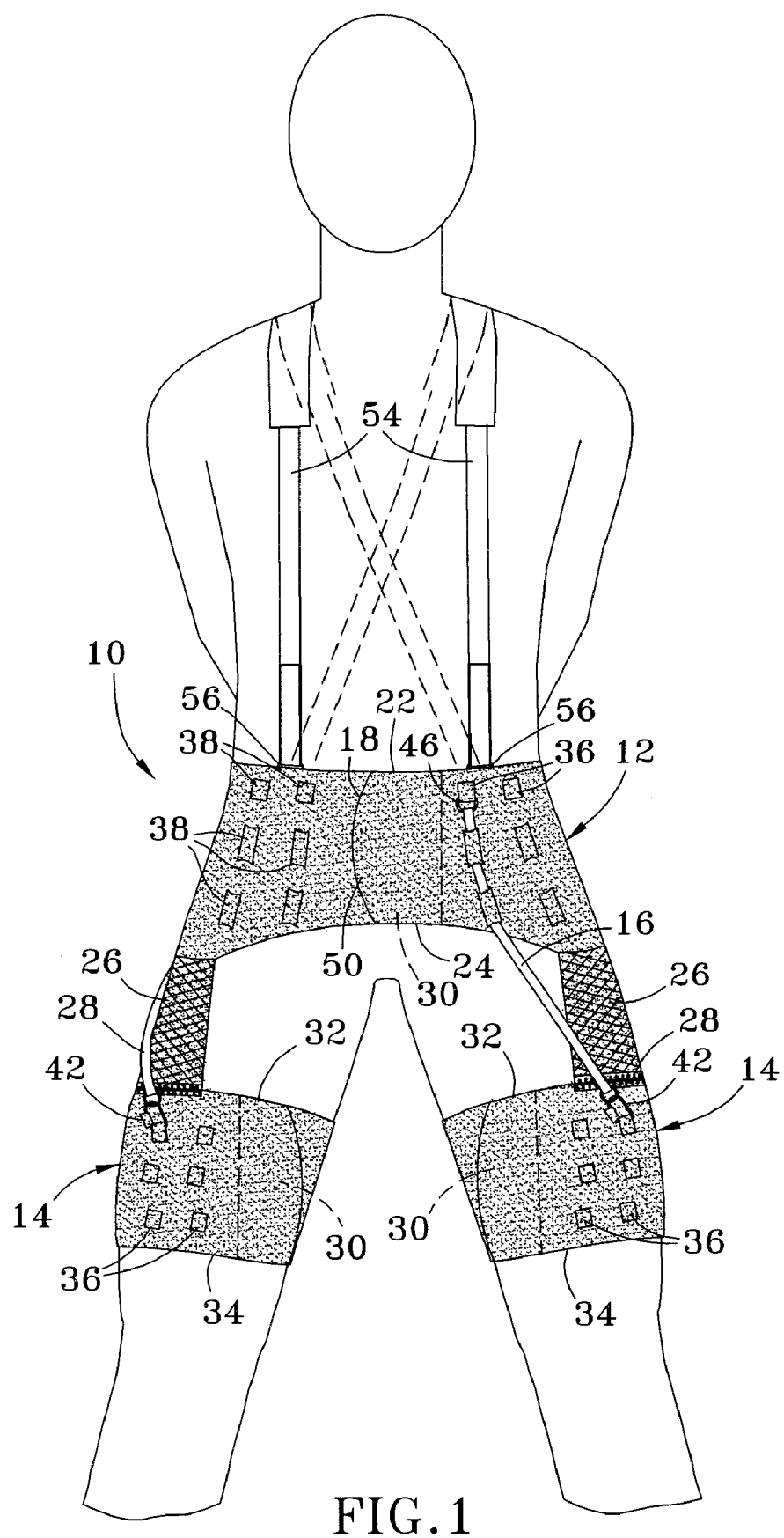
FIGS. 1, 2 and 3 represent anterior, lateral and posterior views, respectively, of a patient wearing a pelvic girdle and two thigh cuffs that cooperate to form a dynamic hip stabilizer in accordance with a preferred embodiment of the invention.

FIGS. 1 through 5 show a dynamic hip stabilizer 10 in accordance with the present invention. The hip stabilizer 10 is shown as including a pelvic girdle 12 and two thigh cuffs 14. The girdle 12 is shown as being elastically interconnected to each thigh cuff 14 with elastic cables 16. The cables 16 are shown connected to the girdle 12 and the thigh cuffs 14 so that, when the hip stabilizer 10 is worn, the cables 16 cooperate to generate an elastic tensile force between the girdle 12 and the cuffs 14. As will be discussed in more detail below, a preferred aspect of the invention is that this elastic tensile force serves to hold the wearer's thigh to the wearer's pelvis with sufficient tension to prevent hip dislocations by controlling excessive adduction, flexion and/or extension, control excessive internal or external rotation, and promote hip stability by controlling and modifying certain hip motions through increasing tension as the extremes of a particular motion are approached, and through constantly maintaining elevated abductor tension. In some patients, the above capabilities may be sufficiently achieved with only one of the thigh cuffs 14 in place.

The girdle 12 and thigh cuffs 14 preferably comprise a flexible but firm outer layer 18 of fabric material sewn or adhered to an inner lining material 20 that is preferably soft and nonirritating to the skin. The outer layer 18 is preferably relatively stiffer than the inner lining material 20 to provide support to the lining material 20. The inner lining material 20 preferably has a high skin friction equivalent, i.e., resists slippage against the skin, a particularly suitable example of which is a synthetic fleece fabric commercially available from Maiden Mills Industries, Inc., under the name POLARFLEECE®. A suitable material for the outer layer 18 is a plastic-molded polyester mesh.

As evident from FIGS. 1 through 5, the girdle 12 is narrower at an upper opening defined by its upper extent 22 (corresponding to the waist level of the wearer) and wider at a lower opening defined by its lower extent 24 (corresponding to the pelvic-hip level of the wearer), so as to have a frustroconical shape. As shown, the inner lining material 20 may project beyond the upper extent 22 of the girdle 12 for added comfort to the wearer. Similar to the girdle 12, each of the thigh cuffs 14 is frustroconical-shaped, though inverted relative to the girdle 12 so as to be wider at an upper opening defined by its proximal-top extent 32 and narrower at a lower opening defined by its inferior-bottom extent 34 in accordance with the shape of the human thigh. With this arrangement, the girdle 12 and thigh cuffs 14 are inhibited from moving toward each other under the elastic tensile force generated by the cables 16. The girdle 12 and the thigh cuffs 14 are preferably closable with hook-and loop-closures 30 (or another suitable releasable fasteners), so that the upper and lower openings of the girdle 12 and thigh cuffs 14 can be appropriately sized for the wearer. The closures 30 of the thigh cuffs 14 are preferably located over the inside of the wearer's thighs when the stabilizer 10 is worn.

As noted above, the cables 16 are intended to reduce the risk of hip dislocations by generating an elastic tensile force between the girdle 12 and thigh cuffs 14 that is sufficient to hold the wearer's thigh to the wearer's pelvis. While a wide variety of elements and materials a capable of providing this tensioning function, a preferred configuration for the cables 16 is a round tubing formed of a rubber material. The desired tensile forces to be generated by the cables 16 will depend on the particular lengths, widths/diameters, and materials of the cables 16, and can be ascertained with minimal trial and error by those skilled in the art. It is believed that a combined elastic tensile force of at least 40 N between the girdle 12 and thigh cuffs 14 is preferred to notably reduce the risk of hip dislocations. It is further believed that a particularly effective hip stabilizer 10 can be achieved with the use of about two to about four cables 16, each generating a tensile force of about 10 to about 20 N to produce a combined elastic tensile force of about 40 to about 60 N between the girdle 12 and thigh cuffs 14.

Extensions 26 of the inner lining material 20 are shown as projecting below the outer layer 18 at the lateral portions of the girdle 12 to extend distally along the midlateral of each thigh, preferably for about three to about five inches (about eight to about thirteen cm) below the outer layer 18. The extensions 26 are represented as being releasably connected to the thigh cuffs 14 with zippers 28, though other releasable fasteners are also within the scope of this invention, as is permanent attachment of the extensions 26 to the thigh cuffs 14. The extensions 26 serve to inhibit slippage and motion between the wearer and the stabilizer 10, inhibit hip flexion, limit rotation of the thigh cuffs 14 when under elastic rotational tension, and help maintain the distance relationship between the girdle 12 and cuffs 14.

As evident from FIGS. 1 through 4, the girdle 12 and thigh cuffs 14 are equipped with one or more series of loops 36. A single transverse row of loops 36 is shown as located near the upper extent 22 of the girdle 12, extending around nearly the full circumference of the girdle 12 while avoiding the hook-and-loop closure 30 (FIG. 1). The transverse loops 36 of the girdle 12 are preferably spaced apart about every two and one-half inches (about six cm). FIGS. 1 through 4 show each thigh cuff 14 as being provided with three rows of the transverse loops 36 vertically spaced apart in the longitudinal direction of the stabilizer 10, with each row extending about three quarters of the circumference of each thigh cuff 14 to avoid the hook-and-loop closures 30 located at the inner thigh. While the girdle 12 is shown with a single transverse row of loops 36 and the thigh cuffs 14 are shown with three transverse rows of loops 36, any number of rows and loops 36 could be used. In particular, the lower row of loops 36 on the cuffs 14 are believed to be optional, as under certain conditions a cable 16 attached to a loop 36 near the lower extent 34 of a cuff 14 may cause the cuff 14 to curl toward the girdle 12. Finally, the loops 36 of the girdle 12 and cuffs 14 need not be aligned in rows.

As also evident from FIGS. 1 through 4, the girdle 12 is further equipped with a series of channel loops 38, shown as being arranged in longitudinal rows that are aligned with the transverse loops 36 and extend toward the lower extent 24 of the girdle 12 and thigh cuffs 14. The channel loops 38 can be formed of fabric to be of any suitable size, e.g., one and one-eighth inches (about 2.8 cm) wide and one and one-quarter inches (about 3.2 cm) long. While shown as raised loops, other channel-type configurations could be used, including more rigid tubes attached to the girdle 12 or channels recessed into or beneath the surface of the girdle 12. Each of the elastic cables 16 is attached to one of the transverse loops 36 of the girdle 12 and to one of the transverse loops 36 of the thigh cuffs 14, passing therebetween through one of the longitudinal rows of channel loops 38 on the girdle 12 so as to be guided and controlled by the channel loops 38.

Figure 2:
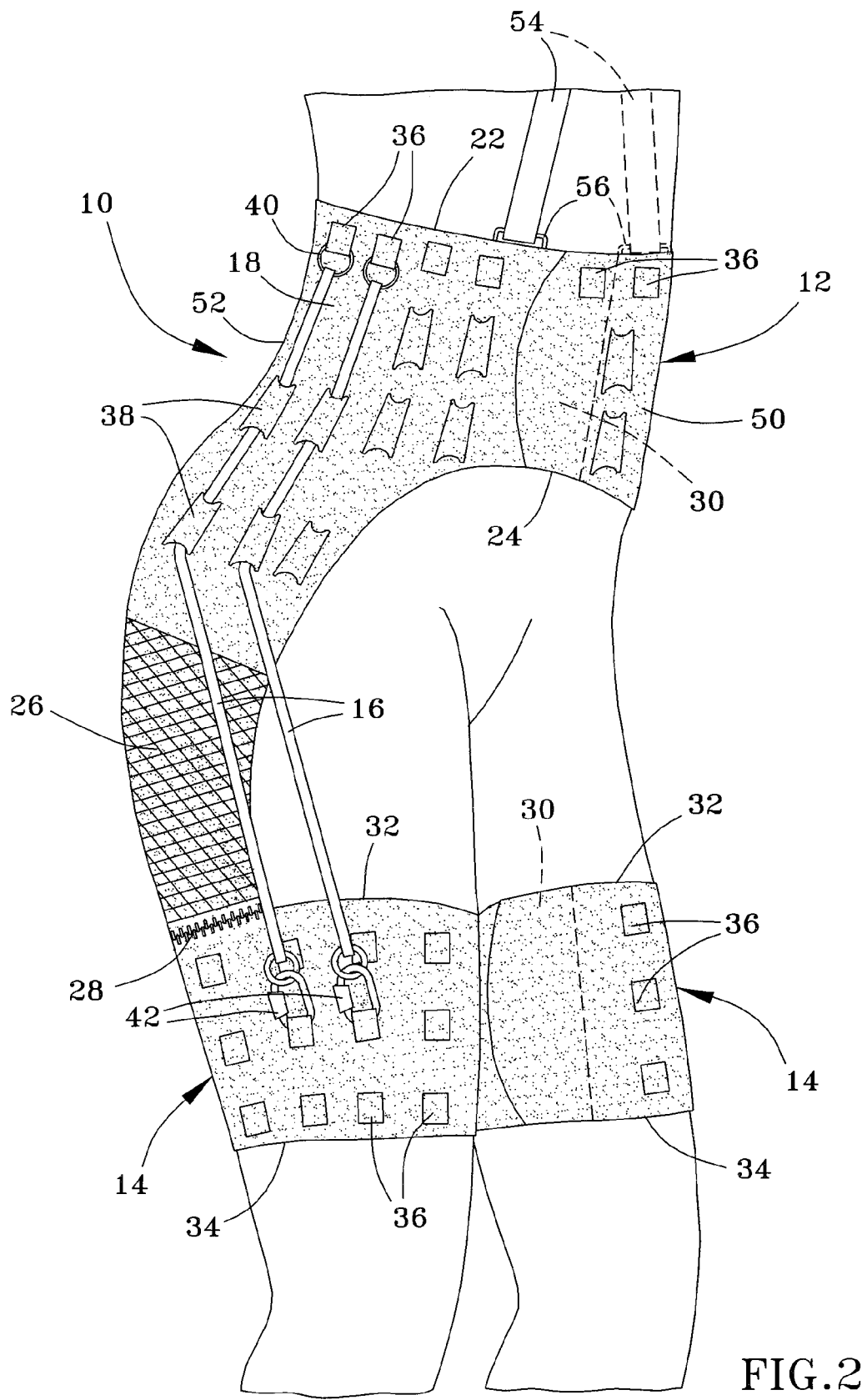
Figure 3:
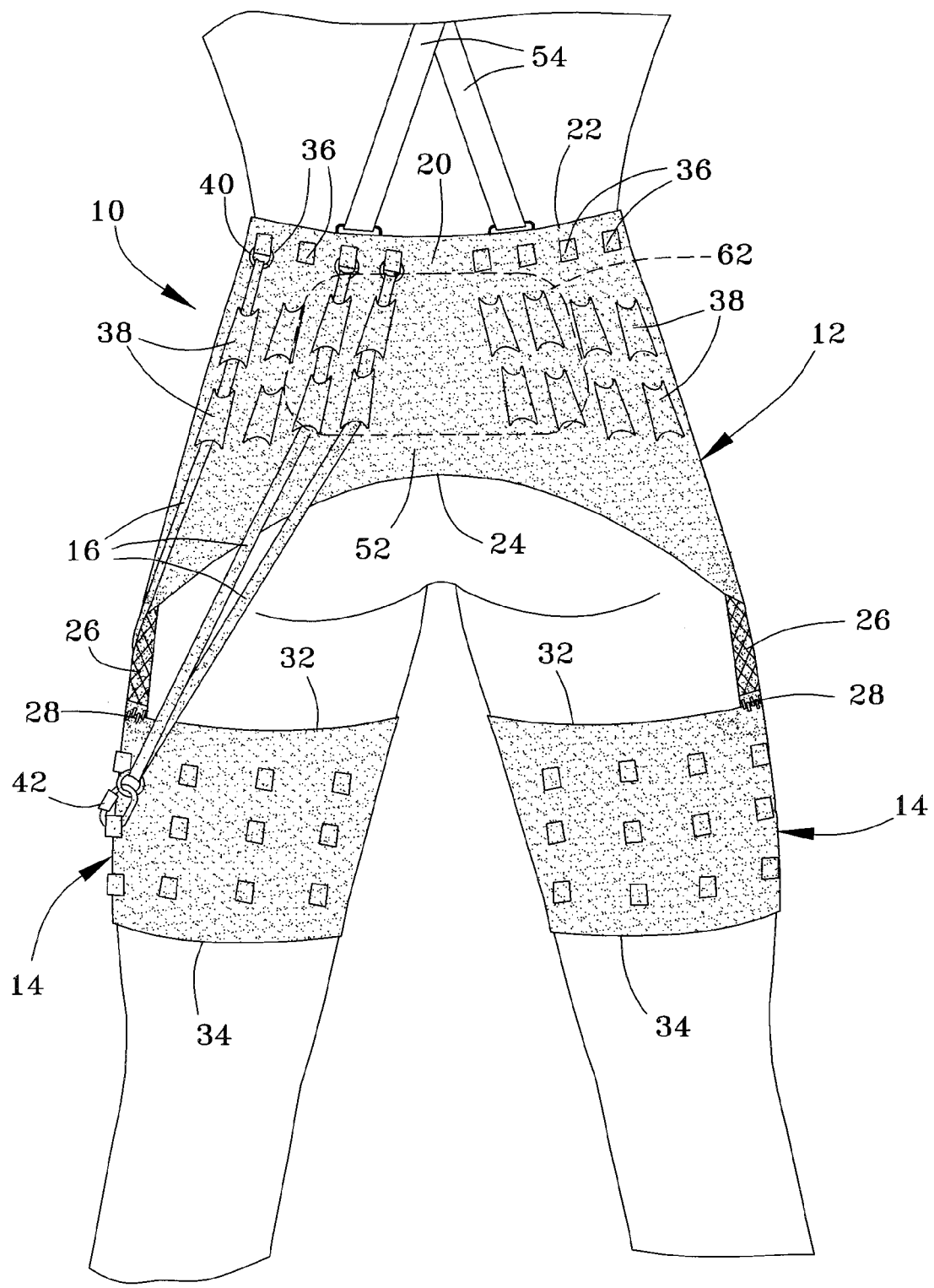

A variety of connector devices can be used to connect the ends of the elastic cables 16 to the transverse loops 36 of the girdle 12 and thigh cuffs 14. In FIGS. 1 through 3, C-shaped rings 40 are shown as connecting the proximal ends of the elastic cables 16 to the transverse loops 36 of the girdle 12, whereas quick links 42 are shown connecting the distal ends of the cables 16 to the transverse loops 36 on the thigh cuffs 14. The quick links 42, well known and commercially available from a variety of sources, are preferably covered with neoprene tubes that act as metal covers. FIG. 6 shows a preferred connector 44 for connecting the cables 16 to the loops 36 of the girdle 12 and thigh cuffs 14. The connector 44 is a D-shaped ring having an arcuate portion 46 and two parallel arms 48. The connector 44 is preferably a zinc oxide-plated steel material, with suitable dimensions being about 16 by 23 mm. The parallel arms 48 are preferably separated by a gap of about 3 mm, which enables the connector 44 to be installed on one of the loops 36 by passing one of the arms 48 under the loop 36, twisting and rotating the connector 44 ninety degrees, and then passing the second arm 48 under the same loop 36. This procedure is believed to be less complicated than what is possible with the C-shaped rings 40 and quick links 42. The preferred D-shaped connector 44 is also potentially stronger and less deformable than comparable C-shaped rings 40.

As evident from FIGS. 1 through 3, the channel loops 38 control the paths of the cables 16, directing the tension generated by the cables 16 along paths beneficial to the wearer. Simultaneously, the loops 38 prevent the cables 16 from moving in directions transverse to the longitudinal direction of the stabilizer 10, which would likely cause discomfort to the wearer. For example, the loops 38 are able to prevent the cables 16 rolling and snapping over the wearer's buttocks or catching in the gluteal cleft. In practice, a single transverse row of channel loops 38 near the lower extent 24 of the girdle 12 has been shown to be adequate, such that the row of channel loops 38 nearest the loops 36 can be considered as optional.

As evident from FIGS. 1 and 3, respectively, cables 16 can be routed between the anterior portion 50 of the girdle 12 and the anterior side of the cuffs 14, and between the posterior portion 52 of the girdle 12 and the posterior side of the cuffs 14. As represented in FIG. 2, cables 16 can also be routed from the posterior portion 52 of the girdle 12 to the anterior or lateral sides of the thigh cuffs 14. Beneficial effects associated with the ability to selectively establish different routes for the cables 16 include the capability of applying internal or external rotational forces. Anterior hip dislocations require an internal rotation and flexion force, while posterior dislocations require external rotation and an extension force. Lateral abductor deficiencies require an abduction force, which can also be generated by appropriately routing one or more cables 16. By varying the tensions and lengths of the cables 16, greater and lesser flexion or extension forces can be created.

In addition to the above features, the hip stabilizer 10 shown in FIGS. 1 through 5 as being equipped with straps 54 attached to the anterior and posterior portions 50 and 52 near the upper extent 22 of the girdle 12. In use, the straps 54 are preferably crossed at the back of the wearer before being passed over the wearer's shoulders. To accommodate wearers of different sizes, the straps 54 are preferably adjustably attached to the anterior 50 of the girdle 12, such as by passing the straps 54 through rings 56 at the upper extent 22, and then folding the straps 54 back onto themselves using, for example, a hook-and-loop attachment (not shown). Each strap 54 is also shown as having a sliding cushioned pad 60 of sufficient length to protect the wearer's shoulders from the pressure of the straps 54. As a result of the shoulder straps 54, the girdle 12 is inhibited from migrating distally toward the thigh cuffs 14 under the influence of the elastic cables 16.

FIGS. 4 and 5 also shown the hip stabilizer 10 as being equipped with an insert 62 that increases the stiffness of the posterior portion 52 of the girdle 12. The insert 62 is preferably sufficiently firm to support the wearer's low back so that stresses from wearing the stabilizer 10 do not result in lower back pain. A suitable insert 62 can be formed of a sheet of firm polymeric material, such as a 3/16 inch (about 5 mm) thick polyethylene sheet. The insert 62 is shown as being received in a pocket 64 (shown partially removed to expose one end of the insert 62) defined on the interior of the girdle 12. A suitable pocket 64 can be formed of the inner lining material 20, and is preferably sized to extend from the upper extent 22 to the lower extent 24 of the girdle 12, and from the mid-lateral line on the left of the wearer, around the back of the girdle 12, to the mid-lateral line on the right of the wearer. The insert 62 is also preferably shaped to be wider (higher) at its ends, allowing a gentle curve over the central gluteal cleft.

The dynamic hip stabilizer 10 as described above is able to solve various problems, shortcomings and disadvantages of the prior art. The stabilizer 10 eliminates motion between the wearer's skin and the stabilizer 10 by using a custom-fitting girdle 12 and thigh cuffs 14 equipped with a soft, high-friction inner lining material 20. With the closures 30, the sizes/circumferences of the girdle 12 and thigh cuffs 14 can be individually tailored to allow for individual abdominal-thigh size variations. The cuffs 14 can then be individually attached to the girdle 12 (e.g., with the zippers 28), thereby inhibiting slippage and motion between the wearer and the stabilizer 10. The elastic cables 16 can be provided in multiple lengths and generate any number of different tensional loads in multiple directions to provide the stabilizing forces required by the wearer's condition. In particular, the cables 16 can be routed between the girdle 12 and the thigh cuffs 14 so that the wearer's thigh is held to the pelvis with enough tension to control excessive adduction, flexion, and/or extension, control excessive internal or external rotation (by passing one or more cables 16 from back to front), provide hip stability by controlling and modifying certain hip motions through increasing tension as the extremes of a particular motion are approached, and provide hip stability by constantly maintaining elevated abductor tension and hip joint compression.

With the dynamic hip stabilizer 10 of this invention, the wearer can be allowed a full range of motion against an increasing tension, which increases strength and institutes proprioceptive feedback to create a muscle contraction throughout the range, thereby aiding the abductor muscles in keeping the hip in place. The constant tension and full range of motion should allow the wearer to move about in bed, sit safely at the side of the bed, and transfer safely to a wheelchair or commode. Unlike various other devices that are commercially available, the stabilizer 10 does not need to be removed for motion or activities. Furthermore, the open groin and buttock areas allow for urination and defecation without having to remove or adjust the stabilizer 10. Finally, the constant and adjustable tension generated by the cables 16 acts as a progressive resistive strengthening device to aid in postoperative rehabilitation.

While the invention has been described in terms of a preferred embodiment, it is apparent that other forms could be adopted by one skilled in the art. For example, the pelvic girdle 12 and thigh cuffs 14 could be formed of a variety of different materials, used alone or in combination. Furthermore, the tension-generating function of the cables 16 can be achieved with elements having a variety of forms, including other tubular-shaped elements, flat elements such as straps, etc. In addition, the 12 girdle could be in the form of a compression or plain pair of shorts with some form of tension-generating elements attached, and the extensions 26 could be eliminated. Therefore, the scope of the invention is to be limited only by the following claims.

The invention claimed is:

1. A dynamic hip stabilizer for reducing the risk of hip dislocation of a wearer, the stabilizer comprising:
   a pelvic girdle having an upper portion configured for defining an upper opening for the wearer's waist, a lower portion configured for defining a lower opening for the wearer's hips, and a posterior portion between midlateral lines of the pelvic girdle and configured for engaging the wearer's lower back when the pelvic girdle is worn by the wearer;
   at least one thigh cuff defining lower and upper openings for the wearer's thigh;
   means for generating an elastic tensile force between the pelvic girdle and the thigh cuff in a longitudinal direction of the dynamic hip stabilizer so as to hold the wearer's thigh to the wearer's pelvis;
   means for engaging the wearer's shoulders to limit movement of the pelvic girdle toward the thigh cuff caused by the elastic tensile force; and
   means for stiffening the posterior portion of the pelvic girdle relative to the upper and lower portions of the pelvic girdle, the stiffening means being centrally disposed in the posterior portion between the mid-lateral lines on the pelvic girdle;
   wherein the only elastic tension applied in the longitudinal direction by the dynamic hip stabilizer is between the pelvic girdle and the at least one thigh cuff so as to hold the wearer's thigh to the wearer's pelvis with sufficient tension to control excessive adduction, flexion or extension, provide hip stability by controlling and modifying hip motions through increasing tension as extremes of the hip motions are approached, and provide hip stability by constantly maintaining elevated abductor tension.

2. The dynamic hip stabilizer according to claim 1, wherein the generating means comprises elastic cables attached to the pelvic girdle and the thigh cuff and extending therebetween so that the cables individually generate portions of the elastic tensile force between the pelvic girdle and the thigh cuff.

3. The dynamic hip stabilizer according to claim 2, further comprising at least one elastic cable passing from the posterior portion of the pelvic girdle to an anterior portion of the thigh cuff, the at least one elastic cable generating an elastic tensile force that controls excessive internal or external rotation.

4. The dynamic hip stabilizer according to claim 2, wherein the generating means further comprises means associated with the pelvic girdle for guiding and controlling movement of the elastic cables in the longitudinal direction of the stabilizer and for inhibiting movement of the elastic cables in directions transverse to the longitudinal direction of the stabilizer.

5. The dynamic hip stabilizer according to claim 4, wherein the guiding and controlling means comprises loops attached to the pelvic girdle and extending in the longitudinal direction of the dynamic hip stabilizer.

6. The dynamic hip stabilizer according to claim 5, wherein the loops are aligned in multiple rows in the longitudinal direction of the dynamic hip stabilizer.

7. The dynamic hip stabilizer according to claim 2, further comprising means for attaching the elastic cables to the pelvic girdle and the thigh cuff, the attaching means providing multiple attachment points for each of the elastic cables on each of the pelvic girdle and the thigh cuff so as to enable selective decreasing and increasing of the portion of the elastic tensile force generated by each of the elastic cables.

8. The dynamic hip stabilizer according to claim 1, further comprising an extension interconnecting the pelvic girdle and the thigh cuff at an outer lateral region of the wearer.

9. The dynamic hip stabilizer according to claim 8, wherein each of the pelvic girdle and the thigh cuff comprises an outer layer of a fabric material overlying an inner layer of a soft lining material, and the extension comprises the soft lining material and is free of the fabric material.

10. The dynamic hip stabilizer according to claim 1, wherein the engaging means comprises shoulder straps attached to the upper portion of the pelvic girdle.

11. The dynamic hip stabilizer according to claim 1, wherein the pelvic girdle and the thigh cuff are each equipped with means for adjusting the sizes of the upper and lower openings thereof.

12. The dynamic hip stabilizer according to claim 1, wherein the stiffening means comprises an insert removably disposed in the posterior portion of the pelvic girdle.

13. The dynamic hip stabilizer according to claim 12, further comprising a pocket in the posterior portion of the pelvic girdle in which the insert is removably disposed.

14. The dynamic hip stabilizer according to claim 1, wherein the stabilizer comprises two of the thigh cuffs.

15. A dynamic hip stabilizer worn by a wearer to reduce the risk of hip dislocation of the wearer, the stabilizer comprising:
   a pelvic girdle comprising an outer layer of a fabric material overlying an inner layer of a soft lining material, the pelvic girdle being narrower at an uppermost extent thereof to define an upper opening for the wearer's waist and being wider at a lowermost extent thereof to define a lower opening for the wearer's hips, and a posterior portion between mid-lateral lines of the pelvic girdle and configured for engaging the wearer's lower back when the pelvic girdle is worn by the wearer;
   means for adjusting the sizes of the upper and lower openings of the pelvic girdle;
   at least one thigh cuff formed of an outer layer of fabric material overlying an inner layer of a soft lining material, the thigh cuff being wider at an uppermost extent thereof to define an upper opening for a thigh of the wearer and being narrower at a lowermost extent thereof to define a lower opening for the wearer's thigh;

an extension interconnecting the pelvic girdle and the thigh cuff at an outer lateral region of the wearer;

means for adjusting the sizes of the upper and lower openings of the thigh cuff;

elastic cables attached to the pelvic girdle and the thigh cuff and individually generating elastic tensile forces between the pelvic girdle and the thigh cuff to inhibit rotation of the pelvic girdle on the wearer, control excessive adduction, flexion and extension, provide hip stability by controlling and modifying hip motions through increasing tension as extremes of a hip motion are approached, and provide hip stability by maintaining elevated abductor tension;

means associated with the pelvic girdle for guiding and controlling movement of the elastic cables in the longitudinal direction of the stabilizer and for inhibiting movement of the elastic cables in directions transverse to the longitudinal direction of the stabilizer during movement of the wearer's hips and the wearer's thighs relative to the wearer's hips;

shoulder straps attached to the upper portion of the pelvic girdle for engaging the wearer's shoulders to limit movement of the pelvic girdle toward the thigh cuff caused by the elastic tensile force; and an insert within the posterior portion of the pelvic girdle, the insert stiffening the posterior portion relative to the upper and lower portions of the pelvic girdle and being centrally disposed in the posterior portion between the mid-lateral lines on the pelvic girdle;

wherein the only elastic tension applied in the longitudinal direction by the dynamic hip stabilizer is between the pelvic girdle and the at least one thigh cuff so as to hold the wearer's thigh to the wearer's pelvis.

16. The dynamic hip stabilizer according to claim 15, wherein at least one of the elastic cables passes from the posterior portion of the pelvic girdle to an anterior portion of the thigh cuff, the elastic tensile force generated by the at least one elastic cable controlling excessive internal or external rotation.

17. The dynamic hip stabilizer according to claim 15, wherein the stabilizer comprises two of the thigh cuffs.

18. The dynamic hip stabilizer according to claim 15, further comprising means for attaching the elastic cables to the pelvic girdle and the thigh cuff, the attaching means providing multiple attachment points for each of the elastic cables on each of the pelvic girdle and the thigh cuff so as to enable selective decreasing and increasing of the elastic tensile force generated by each of the elastic cables.

19. The dynamic hip stabilizer according to claim 18, wherein the attaching means comprises a plurality of loops on the pelvic girdle and the thigh cuff.

20. The dynamic hip stabilizer according to claim 19, wherein the attaching means further comprises rings on the elastic cables, the rings being configured to be selectively attachable to the loops.

21. The dynamic hip stabilizer according to claim 15, wherein the extension comprises the soft lining material of the pelvic girdle and the thigh cuff and is free of the fabric material of the pelvic girdle and the thigh cuff.

22. A dynamic hip stabilizer for reducing the risk of hip dislocation of a wearer, the stabilizer comprising:

a pelvic girdle having an upper portion configured for defining an upper opening for the wearer's waist, a lower portion configured for defining a lower opening for the wearer's hips, and a posterior portion configured for engaging the wearer's lower back when the pelvic girdle is worn by the wearer;

at least one thigh cuff defining lower and upper openings for the wearer's thigh;

means for generating an elastic tensile force between the pelvic girdle and the thigh cuff in a longitudinal direction of the dynamic hip stabilizer so as to hold the wearer's thigh to the wearer's pelvis;

means for engaging the wearer's shoulders to limit movement of the pelvic girdle toward the thigh cuff caused by the elastic tensile force;

means for stiffening the posterior portion of the pelvic girdle relative to the upper and lower portions of the pelvic girdle; and an extension interconnecting the pelvic girdle and the thigh cuff at an outer lateral region of the wearer.

* * * * *